United States Patent [19]

Borzatta et al.

[11] Patent Number: 5,324,834
[45] Date of Patent: Jun. 28, 1994

[54] PIPERIDINE-TRIAZINE CO-OLIGOMERS FOR USE AS STABILIZERS FOR ORGANIC MATERIALS

[75] Inventors: Valerio Borzatta, Bologna; Primo Carrozza, Padova, both of Italy

[73] Assignee: Ciba-Geigy Corporation, Ardsley, N.Y.

[21] Appl. No.: 49,239

[22] Filed: Apr. 16, 1993

Related U.S. Application Data

[63] Continuation of Ser. No. 832,640, Feb. 7, 1992, abandoned, which is a continuation of Ser. No. 712,852, Jun. 10, 1991, abandoned.

Foreign Application Priority Data

Jun. 13, 1990 [IT] Italy ..................... 20631A

[51] Int. Cl.$^5$ ............... C07D 251/00; C07D 413/00; C08K 5/34; C08K 5/35
[52] U.S. Cl. ..................... 544/194; 544/198; 544/209; 544/213; 544/219; 540/554; 540/598; 524/97; 524/100
[58] Field of Search ............... 544/198, 209, 213, 219, 544/194; 540/554, 598; 524/97, 100

[56] References Cited

U.S. PATENT DOCUMENTS

| | | | |
|---|---|---|---|
| 4,086,204 | 4/1978 | Cassandrini et al. | 524/100 |
| 4,331,586 | 5/1982 | Hardy | 524/100 |
| 4,412,020 | 10/1983 | Loffelman et al. | 524/100 |
| 4,459,395 | 7/1984 | Cantatore et al. | 524/100 |
| 4,461,861 | 7/1984 | Loffelman et al. | 524/100 |
| 4,496,726 | 1/1985 | Wiezer et al. | 544/198 |
| 4,547,548 | 10/1985 | Cantatore et al. | 524/100 |
| 4,696,961 | 9/1987 | Cantatore et al. | 524/100 |

FOREIGN PATENT DOCUMENTS

| | | |
|---|---|---|
| 0053775 | 10/1982 | European Pat. Off. |
| 0117229 | 8/1984 | European Pat. Off. |
| 1176662 | 8/1986 | Japan |
| 3196654 | 8/1988 | Japan |

OTHER PUBLICATIONS

Chem. Abst. 102, 7684j.
Chem. Abst. 97, 183468d (1982).

Primary Examiner—Paul R. Michl
Assistant Examiner—Tae H. Yoon
Attorney, Agent, or Firm—Luther A. R. Hall

[57] ABSTRACT

The present invention relates to novel co-oligomers containing recurring units of the formulae (Ia) and (Ib)

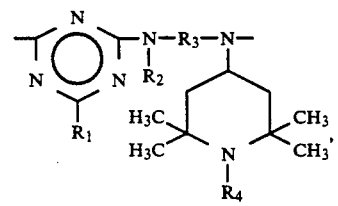

(Ia)

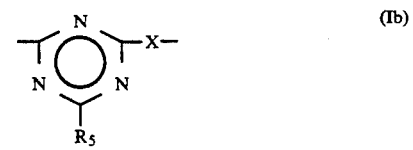

(Ib)

which have a number average molecular weight of e.g. from 1,000 to 5,000 and a (Ia):(Ib) ratio of e.g. 1:1, and in which $R_1$ and $R_5$ are e.g. N-(2,2,6,6-tetramethyl-4-piperidyl)-n-butylamino, $R_2$ is e.g. 2,2,6,6-tetramethyl-4-piperidyl, $R_3$ is e.g. hexamethylene, $R_4$ is e.g. hydrogen and X is e.g. a group

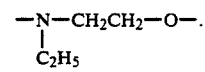

These compounds are particularly suitable for stabilizing organic materials against light, heat and oxidation.

8 Claims, No Drawings

NOVEL PIPERIDINE-TRIAZINE CO-OLIGOMERS FOR USE AS STABILIZERS FOR ORGANIC MATERIALS

This is a continuation of application Ser. No. 07/832,640, filed on Feb. 7, 1992, now abandoned, which is a continuation of application Ser. No. 07/712,852, filed on Jun. 10, 1991, now abandoned.

The present invention relates to novel piperidine-triazine compounds, to their use as light stabilizers, heat stabilizers and oxidation stabilizers for organic materials, in particular synthetic polymers, and to organic materials thus stabilized.

It is known to use triazine oligomers and co-oligomers containing 2,2,6,6-tetramethylpiperidyl groups, as described in U.S. Pat. Nos. 4,086,204, 4,331,586, 4,412,020, 4,459,395, 4,547,548 and 4,696,961, as stabilizers for synthetic polymers.

The present invention relates to novel co-oligomers containing recurring units of the formulae (Ia) and (Ib)

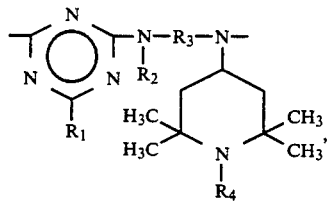

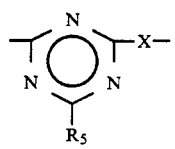

which have a number average molecular weight of from 1,000 to 20,000 and a (Ia):(Ib) ratio of from 4:1 to 1:4, and in which $R_1$ and $R_5$ which can be identical or different are a group $-OR_6$, $-SR_6$ or

in which $R_6$ is hydrogen, $C_1$-$C_{18}$alkyl, $C_5$-$C_{12}$cycloalkyl unsubstituted or mono-, di- or tri-substituted by $C_1$-$C_4$alkyl; $C_3$-$C_{18}$alkenyl, $C_7$-$C_9$phenylalkyl unsubstituted or mono-, di- or tri-substituted on the phenyl by $C_1$-$C_4$alkyl; phenyl which is unsubstituted or mono-, di- or tri-substituted by $C_1$-$C_4$alkyl or $C_1$-$C_4$alkoxy; or a group of the formula (II)

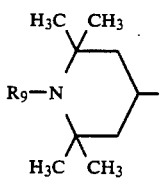

in which $R_9$ is hydrogen, $C_1$-$C_8$alkyl, O, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl unsubstituted or mono-, di- or tri-substituted on the phenyl by $C_1$-$C_4$alkyl; or $C_1$-$C_8$acyl, and $R_7$ and $R_8$ which can be identical or different are as defined above for $R_6$ or are $C_2$-$C_4$alkyl substituted in the 2-, 3- or 4-position by $C_1$-$C_8$alkoxy or by di-($C_1$-$C_4$alkyl)-amino; or

is a 5-membered to 7-membered heterocyclic group, $R_2$ is hydrogen, $C_1$-$C_{18}$alkyl, $C_5$-$C_{12}$cycloalkyl unsubstituted or mono-, di- or tri-substituted by $C_1$-$C_4$alkyl; $C_7$-$C_9$phenylalkyl unsubstituted or mono-, di-or tri-substituted on the phenyl by $C_1$-$C_4$alkyl; or a group of the formula (III)

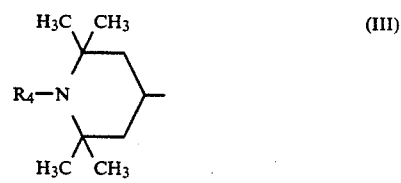

$R_4$ being as defined for $R_9$, $R_3$ is $C_2$-$C_{12}$alkylene, $C_4$-$C_{12}$ alkylene interrupted by 1,2 or 3 oxygen atoms or by 1 or 2 >N—$R_{10}$ groups with $R_{10}$ being as defined above for $R_2$; cyclohexylene, cyclohexylenedimethylene, methylenedicyclohexylene, isopropylidenedicyclohexylene or xylylene, and X is one of the groups of the formulae (IVa)–(IVc)

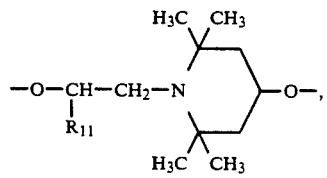

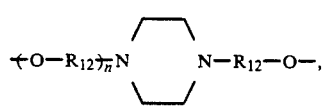

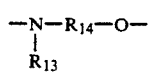

in which $R_{11}$ is hydrogen or $C_1$-$C_8$alkyl, $R_{12}$ is $C_2$-$C_6$alkylene, n is zero or 1, $R_{13}$ is as defined for $R_7$ and $R_8$, and $R_{14}$ is $C_2$-$C_6$alkylene or $C_4$-$C_{12}$alkylene interrupted by 1,2 or 3 oxygen atoms.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by $C_1$-$C_8$alkoxy, preferably $C_1$-$C_4$alkoxy, especially methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$-$C_{18}$alkoxy $R_4$ and $R_9$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$Alkoxy, in particular heptoxy or octoxy, is preferred.

Examples of the various $C_5$-$C_{12}$cycloalkyl substituents which are unsubstituted or mono-, di- or tri-substituted by $C_1$-$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl; unsubstituted or $C_1$-$C_4$alkyl-substituted cyclohexyl is preferred.

Representative examples of $C_5$-$C_{12}$cycloalkoxy $R_4$ and $R_9$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, hexenyl, decenyl, undecenyl and oleyl. Alkenyl groups in which the carbon atom in the 1-position is saturated are preferred; allyl is particularly preferred.

Examples of substituted phenyl are methylphenyl, dimethylphenyl, trimethylphenyl, t-butylphenyl, di-t-butylphenyl, 3,5-di-t-butyl-4-methylphenyl, methoxyphenyl and ethoxyphenyl.

Examples of the various $C_7$-$C_9$phenylalkyl substituents which are unsubstituted or mono-, di- or tri-substituted on the phenyl by $C_1$-$C_4$alkyl are benzyl, methylbenzyl, dimethylbenzyl, trimethylbenzyl, t-butybenzyl and 2-phenylethyl. Benzyl is preferred.

Acyl $R_4$ and $R_9$ having not more than 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonoyl. $C_1$-$C_8$Alkanoyl, $C_3$-$C_8$-alkenoyl and benzoyl are preferred. Acetyl is particularly preferred.

A 5-membered to 7-membered heterocyclic group

can contain a further heteroatom, for example nitrogen or oxygen; representative examples are 1-pyrrolidyl, 1-piperidyl, 4-morpholinyl, 4-methyl-1-piperazinyl and 1-hexahydroazepinyl. 4-Morpholinyl is preferred.

Examples of alkylene having not more than 12 carbon atoms are ethylene, propylene, trimethylene, tetramethylene, pentamethylene, 2,2-dimethyltrimethylene, hexamethylene, trimethylhexamethylene, octamethylene, decamethylene and dodecamethylene.

Examples of $C_4$-$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Representative examples of $C_4$-$C_{12}$alkylene $R_3$ interrupted by 1 or 2>N—$R_{10}$ groups are the groups

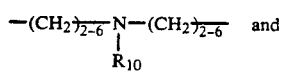 and

-continued

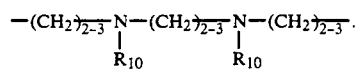

The preferred definitions of $R_4$ and $R_9$ are hydrogen, $C_1$-$C_4$alkyl, OH, $C_6$-$C_{12}$alkoxy, $C_5$-$C_8$cycloalkoxy, allyl, benzyl or acetyl, in particular hydrogen or methyl.

Those co-oligomers are preferred which contain recurring units of the formulae (Ia) and (Ib) and have a number average molecular weight of from 1,000 to 15,000 and a (Ia):(Ib) ratio of from 4:1 to 1:4, and in which $R_1$ and $R_5$ which can be identical or different are a group —$OR_6$, —$SR_6$ or

$R_6$ is $C_1$-$C_{14}$alkyl, $C_5$-$C_8$cycloalkyl unsubstituted or mono-, di- or tri-substituted by $C_1$-$C_4$alkyl; $C_3$-$C_{12}$alkenyl, benzyl, phenyl or a group of the formula (II), $R_7$ and $R_8$ which can be identical or different are as defined above for $R_6$ or are hydrogen or $C_2$-$C_3$alkyl substituted in the 2- or 3-position by $C_1$-$C_4$alkoxy or by di-($C_1$-$C_4$alkyl)amino; or the group

is 1-pyrrolidyl, 1-piperidyl, 4-morpholinyl, 4-methyl-1-piperazinyl or 1-hexahydroazepinyl, $R_2$ is hydrogen, $C_1$-$C_{12}$alkyl, $C_5$-$C_8$cycloalkyl unsubstituted or mono-, di- or tri-substituted by $C_1$-$C_4$alkyl; benzyl or a group of the formula (III), $R_3$ is $C_2$-$C_{10}$alkylene, $C_4$-$C_{10}$alkylene interrupted by 1, 2 or 3 oxygen atoms or by 1 or 2>N—$CH_3$ groups; cyclohexylene, cyclohexylenedimethylene, methylenedicyclohexylene, isopropylidenedicyclohexylene or xylylene, and X is one of the groups of the formulae (IVa)-(IVc) in which $R_{11}$ is hydrogen or $C_1$-$C_4$alkyl, $R_{12}$ is $C_2$-$C_6$alkylene, n is zero or 1, $R_{13}$ is as defined for $R_7$ and $R_8$, and $R_{14}$ is $C_2$-$C_6$alkylene or $C_4$-$C_{10}$alkylene interrupted by 1, 2 or 3 oxygen atoms.

Those co-oligomers are particularly preferred which contain recurring units of the formulae (Ia) and (Ib) and have a member average molecular weight of from 1,000 to 10,000 and a (Ia):(Ib) ratio of from 3:1 to 1:3, and in which $R_1$ and $R_5$ which can be identical or different are a group —$OR_6$, —$SR_6$ or

$R_6$ is $C_1$-$C_{12}$alkyl, cyclohexyl which is unsubstituted or mono-, di or tri-substituted by $C_1$-$C_4$alkyl; allyl, undecenyl, benzyl, phenyl or a group of the formula (II), $R_7$ and $R_8$ which can be identical or different are as defined for $R_6$ or are hydrogen or $C_2$-$C_3$alkyl substituted in the 2- or 3-position by $C_1$-$C_4$alkoxy, by dimethylamino or by diethylamino; or the group

is 4-morpholinyl, $R_2$ is hydrogen, $C_1$-$C_8$alkyl, cyclohexyl which is unsubstituted or mono-, di- or tri-substituted by $C_1$-$C_4$alkyl; benzyl or a group of the formula (III), $R_3$ is $C_2$-$C_8$alkylene, $C_6$-$C_{10}$alkylene interrupted by 2 or 3 oxygen atoms; cyclohexylenedimethylene, methylenedicyclohexylene or xylylene, and X is one of the groups of the formulae (IVa)–(IVc) in which $R_{11}$ is hydrogen or methyl, $R_{12}$ is $C_2$-$C_4$alkylene, n is zero or 1, $R_{13}$ is as defined for $R_7$ and $R_8$, and $R_{14}$ is $C_2$-$C_4$alkylene or $C_4$-$C_8$alkylene interrupted by 1 or 2 oxygen atoms.

Those co-oligomers are of special interest which contain recurring units of the formulae (Ia) and (Ib) and have a number average molecular weight of from 1,000 to 8,000 and a (Ia):(Ib) ratio of from 2:1 to 1:2, and in which $R_1$ and $R_5$ which can be identical or different are a group —$OR_6$ or

$R_6$ is $C_1$-$C_8$alkyl, cyclohexyl, allyl, benzyl, phenyl or a group of the formula (II), $R_7$ and $R_8$ which can be identical or different are as defined above for $R_6$ or are hydrogen or $C_2$-$C_3$alkyl substituted in the 2- or 3-position by methoxy, by ethoxy, by dimethylamino or by diethylamino; or the group

is 4-morpholinyl, $R_2$ is hydrogen, $C_1$-$C_4$alkyl, cyclohexyl or a group of the formula (III), $R_3$ is $C_2$-$C_6$alkylene, $C_6$-$C_{10}$alkylene interrupted by 2 or 3 oxygen atoms; cyclohexylenedimethylene, methylenedicyclohexylene or xylylene, and X is one of the groups of the formulae (IVa)–(IVc) in which $R_{11}$ is hydrogen or methyl, $R_{12}$ is $C_2$-$C_3$alkylene, n is zero or 1, $R_{13}$ is as defined for $R_7$ and $R_8$, and $R_{14}$ is $C_2$-$C_4$alkylene or $C_4$-$C_8$alkylene interrupted by 1 or 2 oxygen atoms.

Those co-oligomers are of particular interest which contain recurring units of the formulae (Ia) and (Ib) and have a number average molecular weight of from 1,000 to 5,000 and a (Ia):(Ib) ratio of from 2:1 to 1:1, and in which $R_1$ and $R_5$ are a group —$OR_6$ or

$R_6$ is $C_1$-$C_4$alkyl, 2,2,6,6-tetramethyl-4-piperidyl or 1,2,2,6,6-pentamethyl-4-piperidyl, $R_7$ and $R_8$ which can be identical or different are $C_1$-$C_8$alkyl, cyclohexyl, 2,2,6,6-tetramethyl-4-piperidyl or 1,2,2,6,6-pentamethyl-4-piperidyl, or $R_7$ can also be hydrogen, or the group

is 4-morpholinyl, $R_2$ is hydrogen, methyl, 2,2,6,6-tetramethyl-4-piperidyl or 1,2,2,6,6-pentamethyl-4-piperidyl, $R_3$ is $C_2$-$C_6$alkylene or $C_8$-$C_{10}$alkylene interrupted by 2 or 3 oxygen atoms, $R_4$ is hydrogen or methyl and X is one of the groups of the formulae (IVa)–(IVc) in which $R_{11}$ is hydrogen, $R_{12}$ is ethylene, n is zero or 1, $R_{13}$ is as defined for $R_7$ and $R_8$, and $R_{14}$ is $C_2$-$C_3$alkylene or $C_4$-$C_6$alkylene interrupted by one oxygen atom.

The novel compounds of the present invention can be prepared by processes known per se, for example as reported in U.S. Pat. No. 4,459,395, by reacting, in the appropriate molar ratios, dichlorotriazines of the formulae (Va) and (Vb)

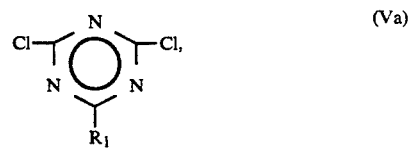

with the compounds of the formulae (VIa) and (VIb)

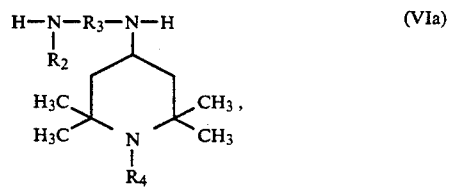

The two reagents (VIa) and (VIb) can be reacted with the dichlorotriazines (Va) and (Vb) simultaneously or separately, using an excess, preferably of not more than 20%, of the reagents (VIa) and (VIb) for controlling the molecular weight. If $R_1 = R_5$ and the (Ia):(Ib) ratio = 1:1, it is possible to prepare co-oligomers having a regular alternation of the recurring units (Ia) and (Ib), first preparing the compound of the formula (VII)

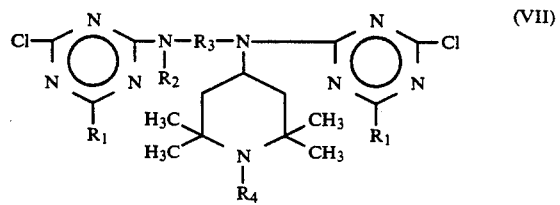

as an intermediate and then reacting it with the compound (VIb).

The reactions are preferably carried out in an aromatic hydrocarbon solvent, for example toluene, xylene or trimethylbenzene, operating at a temperature of e.g. between 40° and 200° C., preferably between 50° and 180° C.

The hydrogen chloride set free in the reaction is preferably neutralized with an inorganic base, for example sodium or potassium hydroxide or carbonate in a quantity at least equivalent to the acid set free.

The dichlorotriazines (Va) and (Vb) can be prepared by known processes by reacting e.g. cyanuric chloride with compounds $R_1$—H and $R_5$—H in equimolar ratio.

If $R_1 = R_5$, the dichlorotriazine thus obtained can be used directly, without isolation from the reaction mixture, for the subsequent reaction with the compounds of the formulae (VIa) and (VIb).

The compounds (VIa) can be prepared, for example, as described in U.S. Pat. No. 4,104,248.

The compounds (VIb) are commercially available or can easily be prepared by known processes.

Depending on the type and the molar ratios of the starting materials (monomers) used, the compounds of the present invention can have different end groups. In particular, the end groups bound to the triazine radical (formulae Ia and Ib) are, for example, —Cl, —OH, —ONa, —OK, a group $R_1$ or $R_5$, with $R_1$ and $R_5$ being as defined above, a group —X—Z or a group

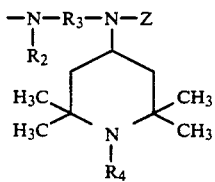

where Z is hydrogen, methyl, $C_1$-$C_8$acyl or ($C_1$-$C_4$alkoxy)-carbonyl. The end group attached to the polyalkylpiperidylimino group (formula (Ia)) and the terminal group attached to the oxygen atom (X of formula (Ib)) are e.g. Z which is as defined above.

If $R_4$ and $R_9 = CH_3$, the co-oligomers of the present invention can preferably be prepared by reacting the corresponding compounds where $R_4$ and $R_9 = H$ with formaldehyde and formic acid or with formaldehyde and hydrogen in the presence of a hydrogenation catalyst such as palladium or platinum.

A preferred embodiment of the instant invention is also a co-oligomer containing recurring units of the formulae (Ia) and (Ib), which has a (Ia):(Ib) ratio of 1:1 and a regular alternation of the recurring units (Ia) and (Ib) characterized in that the co-oligomer contains recurring units of the formula (Ic)

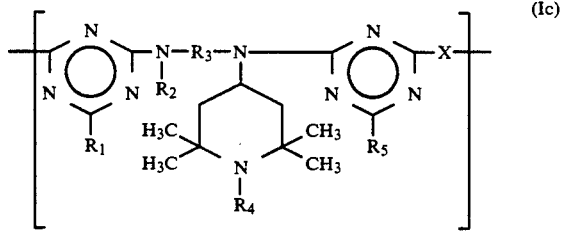

(Ic)

wherein $R_1$ and $R_5$ are identical.

As mentioned in the outset, the novel compounds of the present invention are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$-$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymer of styrene or 60-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene and polyamides.

14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethyleneterephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The instant co-oligomers are particularly suitable for improving the light stability, heat stability and oxidation stability of polyolefins, especially polyethylene and polypropylene.

The co-oligomers of the present invention can be used in mixtures with organic materials in various proportions depending on the nature of the material to be stabilized, on the end use and on the presence of other additives.

In general, it is appropriate to use, for example, 0.01 to 5% by weight of the instant co-oligomers, relative to the weight of the material to be stabilized, preferably 0.05 to 1%.

In general, the instant co-oligomers can be added to the polymeric materials before, during or after the polymerization or crosslinking of the said materials.

The instant co-oligomers can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices. It is possible to incorporate the instant co-oligomers into the material to be stabilized in a pure form or encapsulated in waxes, oils or polymers.

The materials stabilized with the instant co-oligomers can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the instant co-oligomers with the organic materials.

Particular examples of additives which can be used in admixture with the instant co-oligomers are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6- pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis-(1-hydroxy-2,2,6,6-tetramethyl-4-piperidinyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

Several examples of the preparation and use of the co-oligomers containing recurring units of the formulae (Ia) and (Ib) are reported for more detailed illustration of the present invention; these examples are given solely for illustrative purposes and do not imply any restriction. An especially preferred example of the instant invention is example 4.

EXAMPLE 1

A solution of 63.7 g (0.3 mol) of 4-butylamino-2,2,6,6-tetramethylpiperidine in 60 ml of water is added slowly, maintaining the temperature between 0° and 5° C., to a solution of 55.3 g (0.3 mol) of cyanuric chloride in 400 ml of xylene, cooled to 0° C. After 30 minutes, a solution of 12.4 g (0.31 mol) of sodium hydroxide in 30 ml of water is added slowly, maintaining the temperature between 0° and 5° C.

The mixture is stirred for 1 hour at between 5° and 10° C., the aqueous phase is separated off, 59.2 g (0.15 mol) of N,N'-bis-(2,2,6,6-tetramethyl-4-piperidyl)-1,6-hexanediamine and 12 g (0.3 mol) of sodium hydroxide are added, and the whole is heated for 4 hours at 90° C.

40.3 g (0.2 mol) of 1-(2-hydroxyethyl)-2,2,6,6-tetramethyl-4-piperidinol and 24 g (0.6 mol) of ground sodium hydroxide are then added and the mixture is heated for 16 hours under reflux, the water of reaction being separated off azeotropically.

After cooling to about 70° C., the reaction mixture is filtered for separating off the inorganic products, and the filtrate is evaporated under reduced pressure. The product obtained melts at 161°–170° C. and has a molecular weight of $\overline{M}n=3,000$.

EXAMPLES 2–6

Following the procedure described in Example 1 and using the respective reagents in the appropriate molar ratios, the following compounds containing recurring units of the formula

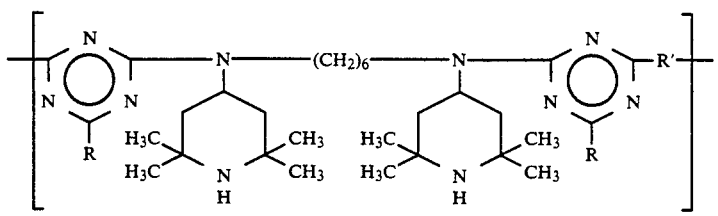

are prepared:.

In the examples, the number-average molecular weight is determined by means of a vapour pressure osmometer (®Gonotec) as described in EP-A-255,990, from page 18, line 54, to page 19, line 15.

| Example | R | R' | m.p. (°C.) | $\overline{M}n$ |
|---|---|---|---|---|
| 2 | n-C₄H₉—N(2,2,6,6-tetramethylpiperidin-4-yl)— | piperazin-1-yl—CH₂CH₂O— | 149–158 | 2100 |
| 3 | n-C₄H₉—N(2,2,6,6-tetramethylpiperidin-4-yl)— | —₂CH₂—N(piperazine)N—CH₂CH₂O— | 130–139 | 4300 |
| 4 | n-C₄H₉—N(2,2,6,6-tetramethylpiperidin-4-yl)— | —N(C₂H₅)—CH₂CH₂O— | 140–147 | 1900 |
| 5 | morpholin-4-yl— | —OCH₂CH₂—N(2,2,6,6-tetramethylpiperidin-4-yl)—O— | 170–177 | 2300 |
| 6 | morpholin-4-yl— | —N(2,2,6,6-tetramethylpiperidin-4-yl)—CH₂CH₂O— | 170–175 | 2000 |

EXAMPLE 7

70.5 g (0.3 mol) of 2,4-dichloro-6-morpholino-1,3,5-triazine, 78.9 g (0.2 mol) of N,N'-bis-(2,2,6,6-tetramethyl-4-piperidyl)-1,6-hexanediamine and 16 g (0.4 mol) of sodium hydroxide in 400 ml of xylene are heated for 4 hours at 70° C.

30.2 g (0.15 mol) of 1-(2-hydroxyethyl)-2,2,6,6-tetramethyl-4-piperidinol and 16 g (0.4 mol) of ground sodium hydroxide are then added, and the mixture is heated for 16 hours under reflux, with the water being separated off azeotropically.

After cooling to about 70° C., the reaction mixture is filtered for separating off the inorganic products, and the filtrate is evaporated under reduced pressure. The product obtained melts at 160°–169° C. and has a molecular weight of $\overline{M}n$ = 2,600.

EXAMPLE 8 light-stabilizing action in polypropylene tapes.

1 g of each of the compounds indicated in Table 1, 1.0 g of tris-(2,4-di-t-butylphenyl)phosphite, 0.5 g of pentaerythritol tetrakis-[3-(3,5-di-t-butyl-4-hydroxyphenyl)-propionate] and 1 g of calcium stearate are mixed in a slow mixer with 1,000 g of polypropylene powder of melt index = 2 g/10 minutes (measured at 230° C. and 2.16 kg).

The mixtures are extruded at 200°–230° C. to give polymer granules which are then converted into stretched tapes of 50 μm thickness and 2.5 mm width, using a pilot-type apparatus (®Leonard-Sumirago (VA) Italy) operating under the following conditions:

| extruder temperature | 210–230° C. |
|---|---|
| head temperature | 240–260° C. |
| stretch ratio | 1:6 |

The tapes thus prepared are exposed, mounted on a white card, in a 65 WR Weather-O-Meter (ASTM D 2565-85) with a black panel temperature of 63° C. The residual tenacity is measured on samples taken after various times of exposure to light by means of a constant-speed tensometer; the exposure time (in hours) ($T_{50}$) needed to halve the initial tenacity is then calculated.

Tapes under the same conditions as indicated above, but without addition of stabilizer are exposed for comparison.

The results obtained are shown in Table 1.

TABLE 1

| Stabilizer | $T_{50}$ (hours) |
|---|---|
| none | 300 |
| compound from Example 1 | 1600 |
| compound from Example 2 | 1800 |

EXAMPLE 9 light-stabilizing action in polypropylene fibres 2.5 g of each of the products indicated in Table 2, 0.5 g of tris-(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1,000 g of polypropylene powder of melt index=12 g/10 minutes (measured at 230° C. and 2.16 kg).

The mixtures are extruded at 200°–230° C. to give polymer granules which are then converted into fibres, using a pilot-type apparatus (®Leonard-Sumirago (VA), Italy), operating under the following conditions:

| extruder temperature | 200–230° C. |
|---|---|
| head temperature | 255–260° C. |
| stretch ratio | 1:3.5 |
| count | 11 dtex per filament. |

The fibres thus prepared are exposed, after mounting on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) need to halve the initial tenacity is then calculated.

Fibres prepared under the same conditions as indicated above, but without the addition of compounds according to the invention, are exposed for comparison.

The results obtained are shown in Table 2:

TABLE 2

| Stabilizer | $T_{50}$ (hours) |
|---|---|
| none | 150 |
| compound from Example 1 | 1060 |
| compound from Example 3 | 1050 |
| compound from Example 5 | 1030 |

TABLE 2-continued

| compound from Example 7 | 1160 |
|---|---|

EXAMPLE 10 antioxidant action in polypropylene plaques 1 g of the compound whose preparation is described in example 4, 0.5 g of octadecyl 3-(3,5-di-t-butyl-4-hydroxyphenyl) propionate, 1 g of tris-(2,4-di-t-butylphenyl) phosphite and 1 g of calcium stearate are mixed in a slow mixer with 1,000 g of polypropylene powder of melt index=2 g/10 minutes (measured at 230° C. and 2.16 kg).

The mixture is extruded twice at 200°–230° C. to give polymer granules which are then converted into plaques of 1 mm thickness by compression-moulding for 6 minutes at 230° C.

The plaques are then punched by means of a DIN 53451 mould, and the specimens obtained are exposed in a forced-circulation air oven maintained at a temperature of 135° C.

The specimens are checked at intervals by folding them by 180°, in order to determine the time (in hours) needed to cause fracture. Speciments prepared under the conditions indicated above, but without addition of the compound of the present invention, are also exposed for comparison.

The results obtained are shown in table 3.

TABLE 3

| Stabilizer | Time to fracture (hrs) |
|---|---|
| none | 550 |
| compound from example 4 | 2160 |

The compounds of the invention can also be used as stabilizers, especially as light stabilizers, for almost all materials known in the art of photographic reproduction and other reproduction techniques as e.g. described in Research Disclosure 1990, 31429 (pages 474 to 480).

What is claimed is:

1. A co-oligomer containing recurring units of the formulae (Ia) and (Ib)

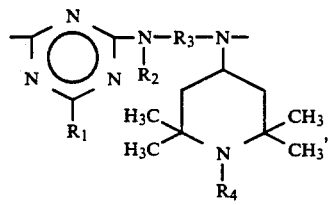 (Ia)

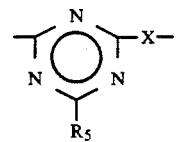 (Ib)

which has a number average molecular weight of from 1,000 to 20,000 and a (Ia):(Ib) ratio of from 4:1 to 1:4, and in which $R_1$ and $R_5$ which can be identical or different are a group —$OR_6$, —$SR_6$ or

in which $R_6$ is hydrogen, $C_1$-$C_{18}$alkyl, $C_5$-$C_{12}$cycloalkyl unsubstituted or mono-, di- or tri-substituted by $C_1$-$C_4$alkyl; $C_3$-$C_{18}$alkenyl, $C_7$-$C_9$phenylalkyl unsubstituted or mono-, di- or tri-substituted on the phenyl by $C_1$-$C_4$alkyl; phenyl which is unsubstituted or mono-, di- or tri-substituted by $C_1$-$C_4$alkyl or $C_1$-$C_4$alkoxy; or a group of the formula (II)

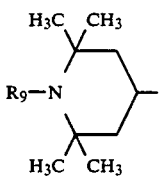

in which $R_9$ is hydrogen, $C_1$-$C_8$alkyl, O., OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl unsubstituted or mono-, di- or tri-substituted on the phenyl by $C_1$-$C_4$alkyl; or $C_1$-$C_8$acyl, and $R_7$ and $R_8$ which can be identical or different are as defined above for $R_6$ or are $C_2$-$C_4$alkyl substituted in the 2-, 3- or 4-position by $C_1$-$C_8$alkoxy or by di-($C_1$-$C_4$alkyl)-amino; or

is a 5-membered to 7-membered heterocyclic group, and $R_5$ is 4-morpholinyl, $R_2$ is hydrogen, $C_1$-$C_{18}$alkyl, $C_5$-$C_{12}$cycloalkyl unsubstituted or mono-, di- or tri-substituted by $C_1$-$C_4$alkyl; $C_7$-$C_9$phenylalkyl unsubstituted or mono-, di- or tri-substituted on the phenyl by $C_1$-$C_4$alkyl; or a group of the formula (III)

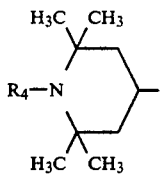

$R_4$ being as defined for $R_9$, $R_3$ is $C_2$-$C_{12}$ alkylene, $C_4$-$C_{12}$ alkylene interrupted by 1, 2 or 3 oxygen atoms or by 1 or 2>N—$R_{10}$ groups with $R_{10}$ being as defined above for $R_2$; cyclohexylene, cyclohexylenedimethylene, methylenedicyclohexylene, isopropylidenedicyclohexylene or xylylene, and X is one of the groups of the formulae (IVa)–(IVc)

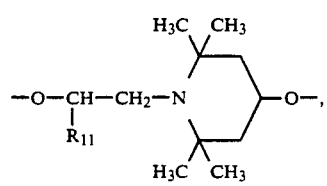

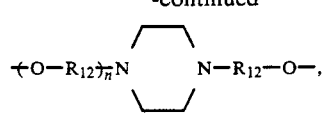

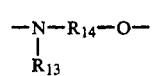

in which $R_{11}$ is hydrogen or $C_1$-$C_8$alkyl, $R_{12}$ is $C_2$-$C_6$alkylene, n is zero or 1, $R_{13}$ is as defined for $R_7$ and $R_8$, and $R_{14}$ is $C_2$-$C_6$alkylene or $C_4$-$C_{12}$alkylene interrupted by 1, 2 or 3 oxygen atoms.

2. A co-oligomer containing recurring units of the formulae (Ia) and (Ib) according to claim 1, in which $R_4$ and $R_9$ which can be identical or different are hydrogen, $C_1$-$C_4$alkyl, OH, $C_6$-$C_{12}$alkoxy, $C_5$-$C_8$cycloalkoxy, allyl, benzyl or acetyl.

3. A co-oligomer containing recurring units of the formulae (Ia) and (Ib) according to claim 1, which has a number average molecular weight of from 1,000 to 15,000 and a (Ia):(Ib) ratio of from 4:1 to 1:4, and in which $R_1$ and $R_5$ which can be identical or different are a group —$OR_6$, —$SR_6$ or

$R_6$ is $C_1$-$C_{14}$alkyl, $C_5$-$C_8$cycloalkyl unsubstituted or mono-, di- or tri-substituted by $C_1$-$C_4$alkyl; $C_3$-$C_{12}$alkenyl, benzyl, phenyl or a group of the formula (II), $R_7$ and $R_8$ which can be identical or different are as defined above for $R_6$ or are hydrogen or $C_2$-$C_3$alkyl substituted in the 2- or 3-position by $C_1$-$C_4$alkoxy or by di-($C_1$-$C_4$alkyl)-amino; or $R_1$ as

is 1-pyrrolidyl, 1-piperidyl, 4-morpholinyl, 4-methyl-1-piperazinyl or 1-hexahydroazepinyl, and $R_5$ is 4-morpholinyl, $R_2$ is hydrogen, $C_1$-$C_{12}$alkyl, $C_5$-$C_8$cycloalkyl unsubstituted or mono-, di- or tri-substituted by $C_1$-$C_4$alkyl; benzyl or a group of the formula (III), $R_3$ is $C_2$-$C_{10}$alkylene, $C_4$-$C_{10}$alkylene interrupted by 1, 2 or 3 oxygen atoms or by 1 or 2>N—$CH_3$ groups; cyclohexylene, cyclohexylenedimethylene, methylenedicyclohexylene, isopropylidenedicyclohexylene or xylylene, and X is one of the groups of the formulae (IVa)--(IVc) in which $R_{11}$ is hydrogen or $C_1$-$C_4$alkyl, $R_{12}$ is $C_2$-$C_6$alkylene, n is zero or 1, $R_{13}$ is as defined for $R_7$ and $R_8$, and $R_{14}$ is $C_2$-$C_6$alkylene or $C_4$-$C_{10}$alkylene interrupted by 1, 2 or 3 oxygen atoms.

4. A co-oligomer containing recurring units of the formulae (Ia) and (Ib) according to claim 1, which has a number average molecular weight of from 1,000 to 10,000 and a (Ia):(Ib) ratio of from 3:1 to 1:3, and in which $R_1$ and $R_5$ which can be identical or different are a group —$OR_6$, —$SR_6$ or

$R_6$ is $C_1$-$C_{12}$alkyl, cyclohexyl which is unsubstituted or mono-, di- or tri-substituted by $C_1$-$C_4$alkyl; allyl, undecenyl, benzyl, phenyl or a group of the formula (II), $R_7$ and $R_8$ which can be identical or different are as defined for $R_6$ or are hydrogen or $C_2$-$C_3$alkyl substituted in the 2- or 3-position by $C_1$-$C_4$alkoxy, by dimethylamino or by diethylamino; or the group

is 4-morpholinyl, $R_2$ is hydrogen, $C_1$-$C_8$alkyl, cyclohexyl which is unsubstituted or mono-, di- or tri-substituted by $C_1$-$C_4$alkyl; benzyl or a group of the formula (III), $R_3$ is $C_2$-$C_8$alkylene, $C_6$-$C_{10}$alkylene interrupted by 2 or 3 oxygen atoms; cyclohexylenedimethylene, methylenedicyclohexylene or xylylene, and X is one of the groups of the formulae (IVa)–(IVc) in which $R_{11}$ is hydrogen or methyl, $R_{12}$ is $C_2$-$C_4$alkylene, n is zero or 1, $R_{13}$ is as defined for $R_7$ and $R_8$, and $R_{14}$ is $C_2$-$C_4$alkylene or $C_4$-$C_8$alkylene interrupted by 1 or 2 oxygen atoms.

5. A co-oligomer containing recurring units of the formulae (Ia) and (Ib) according to claim 1, which has a number average molecular weight of from 1,000 to 8,000 and a (Ia):(Ib) ratio of from 2:1 to 1:2, and in which $R_1$ and $R_5$ which can be identical or different are a group —$OR_6$ or

$R_6$ is $C_1$-$C_8$alkyl, cyclohexyl, allyl, benzyl, phenyl or a group of the formula (II), $R_7$ and $R_8$ which can be identical or different are as defined above for $R_6$ or are hydrogen or $C_2$-$C_3$alkyl substituted in the 2- or 3-position by methoxy, by ethoxy, by dimethylamino or by diethylamino; or the group

is 4-morpholinyl, $R_2$ is hydrogen, $C_1$-$C_4$alkyl, cyclohexyl or a group of the formula (III), $R_3$ is $C_2$-$C_6$alkylene, $C_6$-$C_{10}$alkylene interrupted by 2 or 3 oxygen atoms; cyclohexylenedimethylene, methylenedicyclohexylene or xylylene, and X is one of the groups of the formulae (IVa)–(IVc) in which $R_{11}$ is hydrogen or methyl, $R_{12}$ is $C_2$-$C_3$alkylene, n is zero or 1, $R_{13}$ is as defined for $R_7$ and $R_8$, and $R_{14}$ is $C_2$-$C_4$alkylene or $C_4$-$C_8$alkylene interrupted by 1 or 2 oxygen atoms.

6. A co-oligomer containing recurring units of the formulae (Ia) and (Ib) according to claim 1, which has a number average molecular weight of from 1,000 to 5,000 and a (Ia):(Ib) ratio of from 2:1 to 1:1, and in which $R_1$ and $R_5$ are a group —$OR_6$ or

$R_6$ is $C_1$-$C_4$alkyl, 2,2,6,6-tetramethyl-4-piperidyl or 1,2,2,6,6-pentamethyl-4-piperidyl, $R_7$ and $R_8$ which can be identical or different are $C_1$-$C_8$alkyl, cyclohexyl, 2,2,6,6-tetramethyl-4-piperidyl or 1,2,2,6,6-pentamethyl-4-piperidyl, or $R_7$ can also be hydrogen, or the group

is 4-morpholinyl, $R_2$ is hydrogen, methyl, 2,2,6,6-tetramethyl-4-piperidyl or 1,2,2,6,6-pentamethyl-4-piperidyl, $R_3$ is $C_2$-$C_6$alkylene or $C_8$-$C_{10}$alkylene interrupted by 2 or 3 oxygen atoms, $R_4$ is hydrogen or methyl and X is one of the groups of the formulae (IVa)–(IVc) in which $R_{11}$ is hydrogen, $R_{12}$ is ethylene, n is zero or 1, $R_{13}$ is as defined for $R_7$ and $R_8$, and $R_{14}$ is $C_2$-$C_3$alkylene or $C_4$-$C_6$alkylene interrupted by one oxygen atom.

7. A co-oligomer containing recurring units of the formulae (Ia) and (Ib) according to claim 1, which has a (Ia):(Ib) ratio of 1:1 and a regular alternation of the recurring units (Ia) and (Ib) characterized in that the co-oligomer contains recurring units of the formula (Ic)

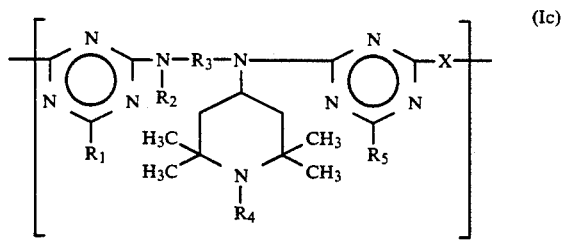

wherein $R_1$ and $R_5$ are identical.

8. A co-oligomer according to claim 7, which has a number average molecular weight of from 1,000 to 5,000 and in which $R_1$ and $R_5$ are N-(2,2,6,6-tetramethyl-4-piperidyl)-n-butylamino, $R_2$ is 2,2,6,6-tetramethyl-4-piperidyl, $R_3$ is hexamethylene, $R_4$ is hydrogen and X is a group

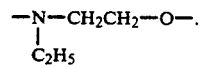

* * * * *